United States Patent [19]

Hosoda et al.

[11] Patent Number: 5,399,772
[45] Date of Patent: Mar. 21, 1995

[54] METHOD OF PRODUCING A 2,4'-DIHYDROXYDIPHENYLSULFONE

[75] Inventors: Masaaki Hosoda; Mikihiko Kurose, both of Fukui; Yoshihiro Sasada, Takefu; Hajime Saito; Masahiro Makino, both of Sabae, all of Japan

[73] Assignee: Nicca Chemical Co., Ltd., Fukui, Japan

[21] Appl. No.: 164,855

[22] Filed: Dec. 10, 1993

[30] Foreign Application Priority Data

May 31, 1993 [JP] Japan .................. 5-152920
May 31, 1993 [JP] Japan .................. 5-152921

[51] Int. Cl.⁶ ............... C07C 315/00; C07C 315/06
[52] U.S. Cl. .................................. 568/33; 568/28
[58] Field of Search ............................ 568/33, 28

[56] References Cited

U.S. PATENT DOCUMENTS

| | | | |
|---|---|---|---|
| 3,318,956 | 5/1967 | Mausner | 568/33 |
| 3,366,692 | 1/1968 | Orem | 568/33 |
| 3,383,421 | 5/1968 | Fox | 568/33 |
| 5,025,090 | 6/1991 | Barda | 568/33 |
| 5,041,677 | 8/1991 | Cooker et al. | 568/33 |
| 5,072,049 | 12/1991 | Stumpp et al. | 568/33 |

FOREIGN PATENT DOCUMENTS

WO8203857 11/1982 WIPO .................. 568/33

*Primary Examiner*—Johann Richter
*Assistant Examiner*—Michael B. Hydorn
*Attorney, Agent, or Firm*—Millen, White, Zelano & Branigan

[57] ABSTRACT

High purity 2,4'-dihydroxydiphenylsulfones useful as developers for thermal recording paper can be produced efficiently and with high selectivity by reacting one or more phenols and sulfuric acid in the presence as of at least one of phosphonic acid, phosphinic acid and salts thereof, in the absence of a solvent or in the presence of an aromatic hydrocarbon solvent having a boiling point at atmospheric pressure of 130° to 200° C., and then purifying the thus-produced crude 2,4'-dihydroxydiphenylsulfones using a mixed solvent containing (1) 5 to 20 weight % of at least one lower aliphatic alcohol and 95 to 80 weight % of at least one aromatic hydrocarbon which does not contain halogen, (2) 10 to 40 weight % of at least one ketone and 90 to 60 weight % of at least one aromatic hydrocarbon which does not contain halogen or (3) 10 to 40 weight % of at least one ester of acetic acid and 90 to 60 weight % of at least one aromatic hydrocarbon which does not contain halogen.

20 Claims, No Drawings

METHOD OF PRODUCING A 2,4'-DIHYDROXYDIPHENYLSULFONE

BACKGROUND OF THE INVENTION

1. Field of the invention

The present invention relates to a novel method of producing a 2,4'-dihydroxyphenylsulfone. More particularly, it relates to a method of producing a 2,4'-dihydroxydiphenylsulfone useful as developer for thermal recording paper efficiently and with high selectivity from phenol or a mixture of phenols and sulfuric acid.

The present invention also relates to a novel method of producing a high purity 2,4'-dihydroxydiphenylsulfone. More particularly, it relates to a method of producing a high purity 2,4'-dihydroxydiphenylsulfone useful as developer for thermal recording paper efficiently by purifying a crude 2,4'-dihydroxydiphenylsulfone produced from phenol or a mixture of phenols and sulfuric acid.

2. Description of the Prior Art

Various kinds of phenol compounds have heretofore been proposed as developer for thermal recording paper. Among the phenol compounds, 2,4'-dihydroxydiphenylsulfones have been expected to provide very useful developer for thermal recording paper.

Method: 4,4'-dihydroxydiphenylsulfones have heretofore been studied extensively and much efforts have been made to obtain high purity 4,4'-dihydroxydiphenylsulfones by minimizing formation of 2,4'-dihydroxydiphenylsulfones which are isomers thereof. However, no method of producing 2,4'-dihydroxydiphenylsulfone in increased yield has heretofore been reported.

When 2,4'-dihydroxydiphenylsulfones are produced in a conventional manner by the reaction of phenols with sulfuric acid, high purity products useful as developer for thermal recording paper have not been obtained. For example, when 2,4'-dihydroxydiplenylsulfone is produced by the reaction of phenol and sulfuric acid, a mixture of isomers containing 2,4'-dihydroxydiphenylsulfone and 4,4'-dihydroxydiphenylsulfone in a weight ratio of about 20 to 80 is obtained even under optimum reaction conditions. When 5-methyl-2,4'-dihydroxydiphenylsulfone is produced by using phenol and p-cresol as the material phenols, or when 3,5-dimethyl-2,4'-dihydroxydiphenylsulfone is produced by using phenol and 2,4'-xylenol as the starting phenol, a product containing at most 10 to 20 weight % of the 2,4'-dihydroxy isomer is obtained in either case.

Purifying 4,4'-dihydroxydiphenylsulfones has heretofore been studied extensively and much effort has been made to obtain high purity 4,4'-dihydroxydiphenylsulfones by minimizing the content of 2,4'-dihydroxydiphenylsulfones which are isomers thereof. However, no method of purifying 2,4'-dihydroxydiphenylsulfones with increased purity has heretofore been reported.

SUMMARY OF THE INVENTION

The present invention accordingly has an object to provide a method of producing a 2,4'-dihydroxydiphenylsulfone with high selectivity and industrially advantageously. The present invention also has an object to provide a method of producing a high purity 2,4'-dihydroxydiphenylsulfone useful as developer for thermal recording :paper efficiently by purifying a crude 2,4'-dihydroxydiphenylsulfone produced from phenols and sulfuric acid.

Extensive investigations were undertaken by the present inventors with the objects described above and it was discovered that 2,4'-dihydroxydiphenylsulfones are produced with high selectivity by heating phenols and sulfuric acid in the presence of a specific catalyst in the absence of a solvent or in the presence of a specific solvent and that high purity 2,4'-dihydroxydiphenylsulfones can be obtained by using a specific solvent for purification. The present invention has been completed on the basis of the discovery.

Thus, the present invention provides a method of producing a 2,4'-dihydroxydiphenylsulfone which comprises reacting by mixing and heating one or more kinds of phenol and sulfuric acid in the presence of at least one compound selected from the group consisting of phosphonic acid, phosphinic acid and salts thereof as catalyst, in the absence of a solvent or in the presence of an aromatic hydrocarbon solvent having a boiling point at atmospheric pressure of 130° to 200° C.

The present invention also provides a method of producing a high purity 2,4'-dihydroxydiphenylsulfone which comprises producing a crude 2,4'-dihydroxydiphenylsulfone by mixing and heating one or more kinds of phenol and sulfuric acid to bring them into reaction with each other in the presence of at least one compound selected from the group consisting of phosphonic acid, phosphinic acid and salts thereof as catalyst, in the absence of a solvent or in the presence of an aromatic hydrocarbon solvent having a boiling point at atmospheric pressure of 130° to 200° C., and purifying the crude 2,4'-dihydroxydiphenylsulfone thus produced using (1) a mixed solvent containing 5 to 20 weight % of at least one kind selected from the group consisting of lower aliphatic alcohols and 95 to 80 weight % of at least one aromatic hydrocarbon not containing halogen, (2) a mixed solvent containing 10 to 40 weight % of at least one ketone and 90 to 60 weight % of at least one aromatic hydrocarbon not containing halogen or (3) a mixed solvent containing 10 to 40 weight % of at least one ester of acetic acid and 90 to 60 weight % of at least one aromatic hydrocarbon not containing halogen.

Other and further objects, features and advantages of the invention will appear more fully from the following description.

DETAILED DESCRIPTION OF THE INVENTION

The invention is described in more detail in the following.

Examples of the phenol used as the starting material in the present invention are those in which at least one of the ortho-positions and the para-position are unsubstituted, such as phenol, o-cresol, m-cresol, 2,3-xylenol, 2,5-xylenol, 3,5-xylenol and the like; mixtures of two kinds thereof; and mixtures of one kind selected from the aforesaid phenols and one kind selected from phenols of which the two ortho-positions or the para-position are substituted, such as p-cresol, 2,4'-xylenol, 2,6-xylenol, 3,4-xylenol and the like.

The phenols are used preferably in a mol ratio to sulfuric acid in the range of 2:1 to 4:1.

In the present invention, the reaction is conducted by heating in the absence of a solvent or in the presence of an aromatic hydrocarbon solvent having a boiling point at atmospheric pressure of 130° to 200° C. in the presence of at least one phosphonic acid, phosphinic acid and salts thereof as catalyst. The amount of the catalyst present in the reaction system is selected generally in the range of 2 weight % or more, preferably 5 to 10 weight %, based on the sulfuric acid. When the amount of the catalyst is less than 2 weight %, the effect of enhancing the selectivity of the reaction to produce the 2,4'-isomer of the dihydroxydiphenylsulfone is not sufficiently exhibited. When the amount is more than 10 weight %, effect of enhancing the selectivity is not correspondingly increased.

When the reaction is conducted in the absence of a solvent, it is preferable that the reaction is conducted by heating to a temperature in the range of 140° to 170° C. under a reduced pressure, preferably of 600 to 50 mmHg. When the reaction is conducted in the presence of a solvent, an aromatic hydrocarbon having a boiling point at atmospheric pressure in the range of 130° to 200° C. is used as the solvent. Examples of the aromatic hydrocarbon solvent are xylene, ethylbenzene, butylbenzene, diethylbenzene, mesitylene, cymene, cumene, pseudocumene, Shellsol A (a product of Shell Chemical Co., an aromatic hydrocarbon mixture solvent comprising 69% of a hydrocarbon having 9 carbon atoms and not comprising halogen), Shellsol AB (a product of Shell Chemical Co., an aromatic hydrocarbon mixture solvent comprising 63% of a hydrocarbon having 10 carbon atoms and not comprising halogen) and the like. The solvent may be used singly or as a combination of two or more kinds. An aromatic petroleum solvent having a boiling at atmospheric pressure in the range of 130° to 200° C. may be used as well.

When the reaction is conducted in the presence of a solvent, the reaction is generally conducted while water formed by the reaction is removed from the reaction system by azeotropic distillation at atmospheric pressure or at a slightly reduced pressure. In the method of production in the presence of the aforesaid solvent, phenolsulfonic acids formed as by-products can be separated from dihydroxydiphenylsulfones easily by filtration. The phenolsulfonic acids and the solvent can be reused.

In the conventional method of producing 4,4'-dihydroxydiphenylsulfone, the amount of a 2,4'-dihydroxy isomer which is formed along with the 4,4'-dihydroxy isomer is about 20 weight % or less when the reaction conditions are such that a mixture of dihydroxydiphenylsulfone isomers is obtained in a yield of 80 mol % or more. Only if, the reaction conditions are adjusted in such a manner that the yield of isomers is decreased to 80 mol % or less does the 2,4'-dihydroxy isomer content increase to 20 weight % or more. Thus, adjustment of the conventional method to a method for the production of a 2,4'-dihydroxydiphenylsulfone causes economically unfavorable results.

In contrast, according to the method of the present invention, the ratio of 2,4'-dihydroxydiphenylsulfone to 4,4'-dihydroxydiphenylsulfone in the reaction product can be increased almost to a weight ratio of 50:50 and the total yield of mixture of dihydroxydiphenylsulfone isomers can also be increased to 80 mol % or more at the same time when phenol is used, for example. As other examples, in the case where a mixture of phenol and p-cresol is used for producing 5-methyl-2,4'-dihydroxydiphenylsulfone or in the case where a mixture of phenol and 2,4-xylenol is used for producing 3,5-dimethyl-2,4'-dihydroxydiphenylsulfone, the 2,4'-dihydroxy isomer content can be increased to 80 weight % or more and the yield of a mixture of the isomers of dihydroxydiphenylsulfone derivatives can be increased to 80 mol % or more at the same time.

A mixture of isomers of a dihydroxydiphenylsulfone obtained by the method of the present invention can be purified to produce a high purity dihydroxydiphenylsulfone.

A crude 2,4'-dihydroxydiphenlylsulfone is treated with a mixed solvent containing (1) 5 to 20 weight % of at least one lower aliphatic alcohol and 95 to 80 weight % of at least one aromatic hydrocarbon not containing halogen, (2) 10 to 40 weight % of at least one ketone and 90 to 60 weight % of at least one aromatic hydrocarbon not containing halogen or (3) 10 to 40 weight % of at least one ester of acetic acid and 90 to 60 weight % of at least one aromatic hydrocarbon not containing halogen.

Examples of the lower aliphatic alcohol which can be used in the mixed solvent (1) are methanol, ethanol, n-propanol, isopropanol, n-butanol, isobutanol, sec-butanol, t-butanol and the like. The lower aliphatic alcohol may be used singly or as a combination of two or more kinds. Examples of an aromatic hydrocarbon not containing halogen are benzene, toluene, xylene, ethylbenzene, butylbenzene. diethylbenzene, mesitylene, cymene, cumene, pseudocumene and the like. The aromatic hydrocarbon not containing halogen may be used singly or as a combination of two or more kinds. When the lower aliphatic alcohol and the aromatic hydrocarbon not containing halogen contents in the mixed solvent (1) are out of the specified ranges, the object of the invention cannot be achieved sufficiently.

Examples of the ketone in the mixed solvent (2) which can be used are acetone, methyl ethyl ketone, methyl isobutyl ketone, 2-pentanone, 3-pentanone, 2-heptanone, 4-heptanone, diisobutyl ketone, cyclohexanone and the like. The ketone may be used singly or as a combination of two or more kinds. Examples of the aromatic hydrocarbon not containing halogen are the same as those described as examples of the aromatic hydrocarbon not containing halogen in the mixed solvent (1). The aromatic hydrocarbon not containing halogen may be used singly or as a combination of two or more kinds. When the ketone and the aromatic hydrocarbon not containing halogen contents in the mixed solvent (2) are out of the specified ranges, the object of the invention cannot be achieved sufficiently.

Examples of the ester of acetic acid in the mixed solvent (3) which can be used are methyl acetate, ethyl acetate, propyl acetate, butyl acetate and the like. The ester of acetic acid may be used singly or as a combination of two or more kinds. Examples of the aromatic hydrocarbon not containing halogen are the same as those described as the examples of the aromatic hydrocarbon not containing halogen in the mixed solvent (1). The aromatic hydrocarbon not containing halogen may be used singly or as a combination of two or more kinds. When the contents of the ester of acetic acid and the aromatic hydrocarbon not containing halogen in the mixed solvent (3) are out of the specified ranges, the object of the invention cannot be achieved sufficiently.

In the method of the present invention, the crude 2,4'-dihydroxydiphenylsulfone obtained by the reaction of the phenol or phenols and the sulfuric acid is added to the mixed solvent described above and dissolved into the solvent by heating. The solution is then cooled and the undissolved portion which contains other isomers, etc. is removed by a conventional method, such as filtration and centrifugal separation. By removing the lower aliphatic alcohol, the ketone or the ester of acetic acid from the remaining solution by distillation, the desired high purity 2,4'-dihydroxydiphenylsulfone can be obtained. In this method, the ratio of mixing the components of the mixed solvent and the amount of the mixed solvent used in the purification can be suitably determined according to the desired purity and the amount of the crude 2,4'-dihydroxydiphenylsulfone for purification. Temperature of the heating and temperature of the cooling can be suitably selected according to the solvent used for the purification.

According to the method of the present invention, it is possible to produce a 2,4'-dihydroxydiphenylsulfone having a purity of 95 weight % or more by suitably selecting the conditions of purification. Furthermore, the method of the present invention does not employ a halogenated hydrocarbon having adverse effects on the environment, such as dichloroethane, o-dichlorobenzene and the like, and can be very advantageously practiced with respect to the environmental health and from the industrial point of view.

To summarize the advantages obtained by the invention: according to the method of the present invention, the isomer of 2,4'-isomer of dihydroxydiphenylsulfones can be obtained efficiently and with high selectivity from phenols and sulfuric acid. By purifying the product with a specific solvent system, high purity 2,4'-dihydroxydiphenylsulfones useful as developer for thermal recording paper can be obtained efficiently. 2,4'-dihydroxydiphenylsulfones are useful as developer for thermal recording paper having good storage property and can be used instead of diaryldihydroxydiphenylsulfones and 4-isopropoxy-4'-hydroxydiphenylsulfone.

The invention will be understood more readily with reference to the following examples; however, these examples are intended to illustrate the invention and are not to be construed to limit the scope of the invention.

EXAMPLE 1

Into a reactor, 793 g of phenol, 334 g of sulfuric acid and 16.5 g of phosphonic acid were charged and a dehydration reaction was conducted under a reduced pressure of 560 to 260 mmHg at 150° to 165° C. for 3 hours with collection of distillate. When the amount of the distillate reached 250 g, 165 g of phenol was added. The dehydration reaction was further continued under a reduced pressure of 260 to 100 mmHg for 2 hours and 180 g of the distillate was obtained. Then, an additional 165 g of phenol were added and the dehydration reaction was continued under a reduced pressure of 260 to 100 mmHg for an additional 2 hours. The reaction was complete when the amount of the distillate reached 140 g. The reaction mixture was washed with water to remove phenolsulfonic acid and then dried. A mixture of dihydroxydiphenylsulfone isomers was obtained in a yield of 85 mol %. Result of analysis by high performance liquid chromatography showed that the product contained 49 weight % of 2,4'-dihydroxydiphenylsulfone, 50 weight % of 4,4'-dihydroxydiphenylsulfone and 1 weight % of other components.

EXAMPLE 2

Into a reactor, 793 g of phenol, 334 g of sulfuric acid and 16.5 g of phosphinic acid were charged and a dehydration reaction was conducted under a reduced pressure of 560 to 260 mmHg at 150° to 165° C. for 3 hours with collection of distillate. When the amount of the distillate reached 240 g, 165 g of phenol was added. The dehydration reaction was further continued under a reduced pressure of 260 to 100 mmHg for 2 hours and 170 g of the distillate was obtained. Then, an additional 165 g of phenol were added and the dehydration reaction was continued under a reduced pressure of 260 to 100 mmHg for additional 2 hours. The reaction was finished when the amount of the distillate reached 125 g. The reaction mixture was washed with water to remove phenolsulfonic acid and then dried. A mixture of dihydroxydiphenylsulfone isomers was obtained with a yield of 82 mol %. Result of analysis by high performance liquid chromatography showed that the product contained 40 weight % of 2,4'-dihydroxydiphenylsulfone, 58 weight % of 4,4'-dihydroxydiphenylsulfone and 2 weight % of other components.

EXAMPLE 3

Into a reactor, 793 g of phenol, 334 g of sulfuric acid, 950 milliliter of mesitylene and 16.5 g of phosphonic acid were charged and a dehydration reaction was conducted under the refluxing condition for 6 hours. The reaction mixture was then cooled to room temperature, filtered to remove phenolsulfonic acid and dried. A mixture of dihydroxydiphenylsulfone isomers was obtained with a yield of 85 mol %. Result of analysis by high performance liquid chromatography showed that the product contained 51 weight % of 2,4'-dihydroxydiphenylsulfone, 48 weight % of 4,4'-dihydroxydiphenylsulfone and 1 weight % of other components.

EXAMPLE 4

Into a reactor, 793 g of phenol, 334 g of sulfuric acid, 950 milliliter of Shellsol A ® and 16.5 g of phosphonic acid were charged. Dehydration reaction was conducted under refluxing conditions for 6 hours. The reaction mixture was then cooled to room temperature, filtered to remove phenolsulfonic acid and dried. A mixture of dihydroxydiphenylsulfone isomers was obtained with a yield of 80 mol %. Result of analysis by high performance liquid chromatography showed that the product contained 52 weight % of 2,4'-dihydroxydiphenylsulfone, 47 weight % of 4,4'-dihydroxydiphenylsulfone and 1 weight % of other components.

EXAMPLE 5

Into a reactor, 793 g of phenol, 334 g of sulfuric acid, 940 g of Shellsol AB ® and 16.5 g of phosphonic acid were charged and a dehydration reaction was conducted under refluxing conditions for 6 hours and a specified amount of water was removed. The reaction mixture was then cooled to room temperature. A crystalline precipitate was separated by filtration, washed and dried. The filtrate was neutralized and washed. After removing the solvent from the filtrate, the remaining product was dried and a crystalline product was obtained. Thus, a mixture of dihydroxydiphenylsulfone isomers was obtained with a yield of 82 mol %. Result of analysis by high performance liquid chromatography showed that the product contained 51 weight % of 2,4'-dihydroxydiphenylsulfone, 47 weight % of 4,4'-dihydroxydiphenylsulfone and 2 weight % of other components.

EXAMPLE 6

Into a reactor, 368 g of p-cresol, 334 g of sulfuric acid, 2000 milliliter of Shellsol A ® and 16.5 g of phosphonic acid were charged and a dehydration reaction was conducted under refluxing conditions for 2 hours. Then, 384 g of phenol were added and the dehydration reaction was continued for an additional 4 hours. The reaction mixture was then cooled to room temperature. A crystalline precipitate was separated, washed with a dilute aqueous alkali solution, then washed with water to remove phenolsulfonic acid and dried. Thus, a mixture of dihydroxydiphenylsulfone isomers was obtained with a yield of 81 mol %. Result of analysis by high performance liquid chromatography showed that the product contained 90 weight % of 5-methyl-2,4'-dihydroxydiphenylsulfone (m.p. 179° C.) and 10 weight % of other components.

EXAMPLE 7

Into a reactor, 416 g of 2,4-xylenol, 334 g of sulfuric acid, 2000 milliliter of Shellsol AB® and 16.5 g of phosphonic acid were charged and a dehydration reaction was conducted under refluxing conditions for 3 hours. Then, 384 g of phenol were added and the dehydration reaction was continued for an additional 4 hours. The reaction mixture was then cooled to room temperature. A crystalline precipitate was separated, washed with a dilute aqueous alkali solution, then washed with water to remove phenolsulfonic acid and dried. Thus, a mixture of dihydroxydiphenylsulfone isomers was obtained with a yield of 80 mol %. Result of analysis by high performance liquid chromatography showed that the product contained 87 weight % of 3,5-dimethyl-2,4'-dihydroxydiphenylsulfone (m.p. 176° C.) and 13 weight % of other components.

Comparative Example 1

Into a reactor, 628 g of phenol and 334 g of sulfuric acid were charged and a dehydration reaction was conducted under a reduced pressure of 560 to 260 mmHg at 150° to 165° C. for 3 hours. When the amount of the distillate reached 160 g, 165 g of phenol were added. The dehydration reaction was further continued under a reduced pressure of 260 to 100 mmHg for 2 hours and 120 g of the distillate were obtained. Then, an additional 120 g of phenol were added and the dehydration reaction was continued under a reduced pressure of 260 to 100 mmHg for additional 2 hours. The reaction was finished when amount of the distillate reached 90 g. The reaction mixture was washed with water to remove phenolsulfonic acid and then dried. A mixture of dihydroxydiphenylsulfone isomers was obtained with a yield of 76 mol %. Result of analysis by high performance liquid chromatography showed that the product contained 18 weight % of 2,4'-dihydroxydiphenylsulfone, 77 weight % of 4,4'-dihydroxydiphenylsulfone and 5 weight % of other components.

EXAMPLE 8

Into a mixed solvent containing 205 g of xylene and 45 g of isopropanol, 100 g of the mixture of dihydroxydiphenylsulfone isomers obtained by the reaction of phenol and sulfuric acid in Example 1 were dispersed and the dispersion was heated to the refluxing condition for 2 hours. The reaction mixture was then cooled to 40° to 30° C. A crystalline precipitate was separated by filtration and dried to obtain 42 g of 4,4'-dihydroxydiphenylsulfone. Isopropanol was removed from Filtrate and a crystalline precipitate was separated by filtration and dried to obtain 53 g of 2,4'-dihydroxydiphenylsulfone. Result of analysis by high performance liquid chromatography showed that purities of 4,4'-dihydroxydiphenylsulfone and 2,4'-dihydroxydiphenylsulfone were 97.0 weight % and 80.5 weight %, respectively.

EXAMPLE 9

Into a mixed solvent containing 220 g of xylene and 30 g of isopropanol, 100 g of the mixture of dihydroxydiphenylsulfone isomers obtained by the reaction of phenol and sulfuric acid in Example 2 were dispersed and the dispersion was heated to the refluxing condition for 2 hours. The reaction mixture was then cooled to 40° to 30° C. A crystalline precipitate was separated by filtration and dried to obtain 45 g of 4,4'-dihydroxydiphenylsulfone. Isopropanol was removed from the filtrate and a crystalline precipitate was separated by filtration and dried to obtain 50 g of 2,4'-dihydroxydiphenylsulfone. Result of analysis by high performance liquid chromatography showed that purities of 4,4'-dihydroxydiphenylsulfone and 2,4'-dihydroxydiphenylsulfone were 97.0 weight % and 75.5 weight %, respectively.

EXAMPLE 10

Into a mixed solvent containing 160 g of xylene and 90 g of methyl ethyl ketone, 100 g of the mixture of dihydroxydiphenylsulfone isomers obtained by the reaction of phenol and sulfuric acid in Example 3 were dispersed and the dispersion was heated to the refluxing condition for 2 hours. The reaction mixture was then cooled to 40° to 30° C. A crystalline precipitate was separated by filtration and dried to obtain 42 g of 4,4'-dihydroxydiphenylsulfone. Methyl ethyl ketone was removed from filtrate and a crystalline precipitate was separated by filtration and dried. After recrystallization from a water/methanol mixed solvent, 43 g of 2,4'-dihydroxydiphenylsulfone was obtained. Result of analysis by high performance liquid chromatography showed that purities of 4,4'-dihydroxydiphenylsulfone and 2,4'-dihydroxydiphenylsulfone were 97.0 weight % and 97.0 weight %, respectively.

EXAMPLE 11

Into a mixed solvent containing 155 g of mesitylene and 95 g of butyl acetate, 100 g of the mixture of dihydroxydiphenylsulfone isomers obtained by the reaction of phenol and sulfuric acid in Example 4 were dispersed and the dispersion was heated to the refluxing condition for 2 hours. The reaction mixture was then cooled to 40° to 30° C. A crystalline precipitate was separated by filtration and dried to obtain 45 g of 4,4'-dihydroxydiphenylsulfone. Butyl acetate was removed from filtrate and a crystalline precipitate was separated by filtration and dried to obtain 41 g of 2,4'-dihydroxydiphenylsulfone. Result of analysis by high performance liquid chromatography showed that purities of 4,4'-dihydroxydiphenylsulfone and 2,4'-dihydroxydiphenylsulfone were 96.5 weight % and 97.0 weight %, respectively.

EXAMPLE 12

Into a mixed solvent containing 150 g of mesitylene and 90 g of methyl isobutyl ketone, 100 g of the mixture of dihydroxydiphenylsulfone isomers obtained by the reaction of phenol, 2,4'-xylenol and sulfuric acid in Example 7 was dispersed and the dispersion were heated to the refluxing condition for 2 hours. The reaction mixture was then cooled to 40° C. or lower and precipitate formed was removed by filtration. Methyl isobutyl ketone was removed from the filtrate to obtain 67 g of 3,5-dimethyl-2,4'-dihydroxydiphenylsulfone. Result of analysis by high performance liquid chromatography showed that purity of the product was 97.5 weight %.

EXAMPLE 13

Into a mixed solvent containing 140 g of xylene and 100 g of butyl acetate, 100 g of the mixture of dihydroxydiphenylsulfone isomers obtained by the reaction of phenol, 2,4'-xylenol and sulfuric acid in Example 7 was dispersed and the dispersion were heated to the refluxing condition for 2 hours. The reaction mixture was then cooled to 40° C. or lower and a precipitate formed, which was removed by filtration. Butyl acetate was removed from the filtrate to obtain 65 g of 3,5-dimethyl-2,4'-dihydroxydiphenylsulfone. Result of analysis by high performance liquid chromatography showed that purity of the product was 97.0 weight %.

What is claimed is:

1. A method of increasing the ratio of 2,4'-isomer to 4,4'-isomer of a dihydroxydiphenylsulfone in a reaction product produced by the dehydration reaction of a phenol or a mixture of phenols with sulfuric acid, which comprises the steps of conducting the dehydration reaction in the presence of at least one of phosphonic acid, phosphinic acid and salts thereof and either in the absence of a solvent or in the presence of an aromatic hydrocarbon solvent having a boiling point at atmospheric pressure of 130° to 200° C., and isolating the thus-produced 2,4'-isomer from the reaction product containing concurrently produced 4,4'-isomer.

2. A method as claimed in claim 1, wherein the reaction is conducted at a temperature of 140° to 170° C. under reduced pressure in the absence of a solvent.

3. A method as claimed in claim 1, wherein the reaction is conducted in the presence of an aromatic hydrocarbon solvent having a boiling point at atmospheric pressure of 130° to 200° C. and water formed by the reaction is removed from the reaction system by azeotropic distillation.

4. A method as claimed in claim 1, wherein the dihydroxydiphenylsulfone is 2,4'-dihydroxydiphenylsulfone obtained by reacting phenol with sulfuric acid.

5. A method as claimed in claim 2, wherein the dihydroxydiphenylsulfone is 2,4'-dihydroxydiphenylsulfone obtained by reacting phenol with sulfuric acid.

6. A method of as claimed in claim 3, wherein the dihydroxydiphenylsulfone is 2,4'-dihydroxydiphenylsulfone obtained by reacting phenol with sulfuric acid.

7. A method as claimed in claim 1, wherein the dihydroxydiphenylsulfone is 5-methyl-2,4'-dihydroxydiphenylsulfone obtained by reacting phenol and p-cresol with sulfuric acid.

8. A method as claimed in claim 2, wherein the dihydroxydiphenylsulfone is 5-methyl-2,4'-dihydroxydiphenylsulfone obtained by reacting phenol and p-cresol with sulfuric acid.

9. A method as claimed in claim 3, wherein the dihydroxydiphenylsulfone is 5-methyl-2,4'-dihydroxydiphenylsulfone obtained by reacting phenol and p-cresol with sulfuric acid.

10. A method as claimed in claim 1, wherein the dihydroxydiphenylsulfone is 3,5-dimethyl-2,4'-dihydroxydiphenylsulfone obtained by reacting phenol and 2,4-xylenol with sulfuric acid.

11. A method as claimed in claim 2, wherein the dihydroxydiphenylsulfone is 3,5-dimethyl-2,4'-dihydroxydiphenylsulfone obtained by reacting phenol and 2,4-xylenol with sulfuric acid.

12. A method as claimed in claim 3, wherein the dihydroxydiphenylsulfone is 3,5-dimethyl-2,4'-dihydroxydiphenylsulfone obtained by reacting phenol and 2,4-xylenol with sulfuric acid.

13. A method as claimed in claim 1 wherein the reaction is conducted in the presence of phosphonic acid.

14. A method as claimed in claim 1 wherein the reaction is conducted in the presence of phosphinic acid.

15. A method of producing in high purity the 2,4'-isomer of the dihydroxydiphenylsulfone which comprises producing a crude 2,4'-dihydroxydiphenylsulfone by by reacting a phenol or a mixture of phenols with sulfuric acid, in the presence of at least one of phosphonic acid, phosphinic acid and salts thereof and in the absence of a solvent or in the presence of an aromatic hydrocarbon solvent having a boiling point at atmospheric pressure of 130° to 200° C. and purifying the crude 2,4'-isomer thus produced by selective solution in a mixed solvent containing 5 to 20 weight % of at least one lower aliphatic alcohol and 95 to 80 weight % of at least one aromatic hydrocarbon which does not contain halogen, cooling the solvent mixture to precipitate the thus-purified 2,4'-isomer therefrom and separating the precipitated 2,4'-isomer from the solvent mixture.

16. A method of producing in high purity the 2,4'-isomer of a dihydroxydiphenylsulfone which comprises producing a crude 2,4'-dihydroxydiphenylsulfone by reacting a phenol or a mixture of phenols with sulfuric acid, in the presence of at least one of phosphonic acid, phosphinic acid and salts thereof and in the absence of a solvent or in the presence of an aromatic hydrocarbon solvent having a boiling point at atmospheric pressure of 130° to 200° C. and purifying the crude 2,4'-isomer thus produced by selective solution in a mixed solvent containing 10 to 40 weight % of at least one ketone and 90 to 60 weight % of at least one aromatic hydrocarbon which does not contain halogen, cooling the solvent mixture to precipitate the thus-purified 2,4'-isomer therefrom and separating the precipitated 2,4'-isomer from the solvent mixture.

17. A method of producing in high purity the 2,4'-isomer of a dihydroxydiphenylsulfone which comprises producing a crude 2,4'-dihydroxydiphenylsulfone by reacting a phenol or a mixture of phenols with sulfuric acid, in the presence of at least one of phosphonic acid, phosphinic acid and salts thereof and in the absence of a solvent or in the presence of an aromatic hydrocarbon solvent having a boiling point at atmospheric pressure of 130° to 200° C. and purifying the crude 2,4'-isomer thus produced by selective solution in a mixed solvent containing 10 to 40 weight % of at least one ester of acetic acid and 90 to 60 weight % of at least one aromatic hydrocarbon which does not contain halogen, cooling the solvent mixture to precipitate the thus-purified 2,4'-isomer therefrom and separating the precipitated 2,4'-isomer from the solvent mixture.

18. A method as claimed in claim 15, wherein said dihydroxydiphenylsulfone is 2,4'-dihydroxydiphenylsulfone obtained by reacting phenol with sulfuric acid 19. A method as claimed in claim 16, wherein said dihydroxydiphenylsulfone is 2,4'-dihydroxydiphenylsulfone obtained by reacting phenol with sulfuric acid 20. A method as claimed in claim 17, wherein said dihydroxydiphenylsulfone is 2,4'-dihydroxydiphenylsulfone obtained by reacting phenol with sulfuric acid.

* * * * *